United States Patent [19]

Winters

[11] 4,412,953
[45] Nov. 1, 1983

[54] PROCESS FOR PREPARING 16α-HYDROXY-17α-AMINOPREGNANE DERIVATIVES

[75] Inventor: Giorgio Winters, Milan, Italy

[73] Assignee: Gruppo Lepetit, S.p.A., Milan, Italy

[21] Appl. No.: 322,485

[22] Filed: Nov. 18, 1981

[30] Foreign Application Priority Data

Nov. 26, 1980 [IT] Italy ............................. 26229 A/80

[51] Int. Cl.³ ............................................. C07J 43/00
[52] U.S. Cl. ............................. 260/239.5; 260/397.45; 260/397.47
[58] Field of Search ..................................... 260/239.5

[56] References Cited

U.S. PATENT DOCUMENTS 3,631,033 12/1971 Nathansohn et al. .......... 260/239.55
4,031,075 6/1977 Woods et al. ............. 260/239.55 D

OTHER PUBLICATIONS

A. I. Terekhina et al., Khim. Farm. Zur, 11, pp. 97–100, (1977), Also Included is a Copy of the Corresponding Derwent Abstract (13005v).
A. A. Akhrem et al., Bull., Acad., Pol. Sci., vol. XII, pp. 929–933, (1974).
G. G. Nathansohn et al., Gazz. Chim., Ital. 95, pp. 1338–1370, (1965).

Primary Examiner—Elbert L. Roberts
Attorney, Agent, or Firm—William J. Stein; Gary D. Street; Raymond A. McDonald

[57] ABSTRACT

A process for preparing 16α-hydroxy-17α-aminopregnane derivatives through the opening of the corresponding 16α, 17α-epoxides with amines.

The use of the thus obtained compounds as intermediates in the synthesis of pharmacologically active pregnano-[17α,16α-d]oxazolines is also claimed.

9 Claims, No Drawings

PROCESS FOR PREPARING 16α-HYDROXY-17α-AMINOPREGNANE DERIVATIVES

The present invention refers to a process for preparing 16α-hydroxy-17α-aminopregnane derivatives represented by the general formula

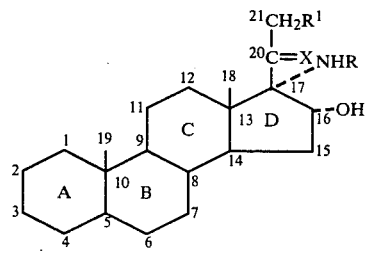

wherein R is hydrogen, alkyl, aralkyl; $R^1$ is hydrogen, hydroxy, alkanoyloxy or aroyloxy, and X is O or an easily removable protecting group of the carbonyl function; rings A, B and C of the pregnane skeleton may be substituted at the 3- and 11-positioned carbon atoms with oxo, hydroxy, alkoxy, aralkoxy and acyloxy functions and bear one or more non-cumulated double bond at positions 1-2, 3-4, 4-5, 5-5, 6-7, and 9-11.

A further object of this invention is the use of the new process of manufacturing 16α-hydroxy-17α-aminopregnanes in the synthesis of pregnano[17α,16α-d]oxazoline derivatives of formula III

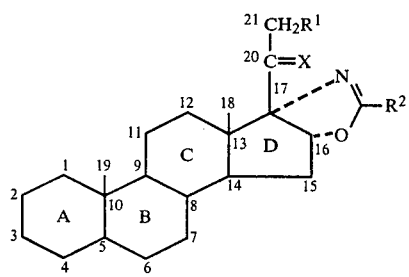

wherein $R^2$ is hydrogen, alkyl, aryl, and aralkyl; $R^1$ and X have the same meanings as above and rings A, B, and C of the pregnane skeleton may be substituted at C-3 and C-11 and bear double bonds as above. Pregnano[1-7α,16α-d]oxazoline derivatives with antiinflammatory and glucocorticoid activity are described in U.S. Pat. Nos. 3,413,286, 3,461,119, and 3,436,389.

According to an embodiment of the present invention, pregnano[17α,16α-d]oxazoline derivatives are prepared from the 16α-hydroxy-17α-aminopregnane derivatives of formula (I) obtained according to the process of the present invention, through reaction with an aliphatic, aromatic or arylaliphatic carboxylic acid of formula $R^2COOH$ or a functional derivative equivalent thereof like an anhydride, an acyl chloride, an ortho-ester, a nitrile, an imidoether, an amide, or an amidine, wherein $R^2$ has the same meanings as above, according to the process described in U.S. Pat. No. 3,413,286.

The process of the present invention is particularly useful for the preparation of those 16α-hydroxy-17α-aminopregnane intermediates which are necessary for obtaining pharmacologically active pregnano[17α,16α-d]-oxazolines.

Some of the compounds of formula (I) which are obtainable through the process of the present invention are new and useful precursors for pregnano-oxazoline derivatives endowed with a remarkable therapeutic activity. These new compounds represent a further specific object of the present invention.

Among the compounds of formula I which are of particular interest as intermediates for pharmacologically active pregnano[17α,16α-d]oxazolines, there are those compounds of formula I wherein R is hydrogen, $R^1$ and X have the same meanings as before, and rings A, B, C may be substituted at C-11 with an oxo, hydroxy or acyloxy group, are substituted at C-3 with a group selected from oxo, hydroxy, alkoxy, aralkoxy, and acyloxy, and may bear one or more noncumulated double bond at the 1-2, 3-4, 4-5, and 5-6 positions.

Examples of compounds of formula I which are of particular interest, are more specifically represented by the following formulas Ia and Ib

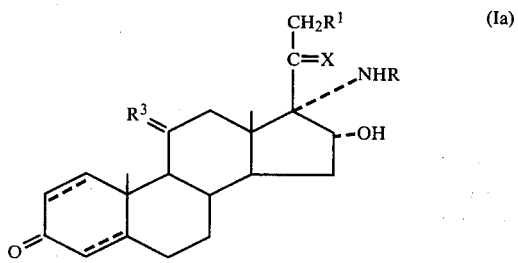

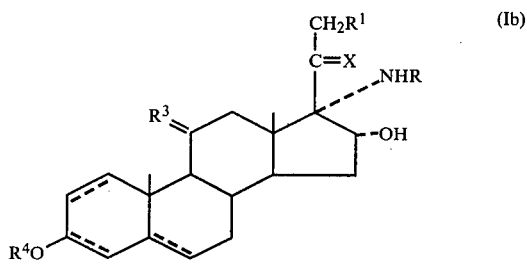

wherein R, $R^1$, and X have the same meanings as before, $R^3$ represents $H_2$, O H(OH), H(O-acyl); $R^4$ represents hydrogen, alkyl, aralkyl, or acyl and the dotted lines represent possible carbon-carbon double bonds in the pregnane skeleton. In particular the compounds of formula Ia and Ib wherein R, $R^1$, X, $R^3$, and $R^4$ are as defined above with the proviso that when R is hydrogen, X must be different from oxygen, are novel and represent a further specific object of the present invention.

In the compounds of formula (I), (Ia), (Ib), and (III), the hydroxy, alkoxy, aralkoxy, or acyloxy substituents, when linked to a saturated carbon atom, may have α-or β-stereochemical configuration, wherein the α, β system is the most commonly used system for denoting stereochemical configuration of substituents attached to the pregnane skeleton.

In the present specification and claims, the term "alkyl" or the alkyl moiety in other groups containing an alkyl portion, as "alkoxy" or "aralkyl" groups, identifies a straight or branched saturated hydrocarbyl group of 1 to 6 carbon atoms, The term "aryl" or the portion "aryl" in the terms "aralkyl" and "aralkoxy" designates a phenyl group optionally substituted with one to three groups independently selected from halogen, alkoxy, nitro, cyano, carboxy, carbalkoxy and trifluoromethyl.

The term "acyl" and the portion "acyl" in the term "acyloxy" identifies an acyl radical derived from an alkanoic or alkylsulfonic acid of from 1 to 8 carbon atoms, an aryloic, arylsulfonic, arylalkanoic or, arylalkyl-sulfonic acid wherein the aryl and alkyl portions are as defined above.

The direct and simultaneous introduction of 16α-hydroxy-17α-amino groups in the pregnane nuclei through the opening of 16α,17α-epoxides is not described in literature.

16α-hydroxy-17α-amino pregnanes have been prepared through the opening of 16α,17α-epoxides by the nucleophilic attack of the $N_3^\ominus$ species and subsequent catalytical reduction of the 17α-azido derivative to amino. See for instance A. I. Terekhina et al., Kim. Farm. Zhur. Vol. 11, page 97, (1977); Russian Patent 380649 (Derwent 13005 V); A. A. Akhrem et al., Bull. Acad. Pol. Sci., Vol. XXIII, page 929, (1974); G. G. Nathansohn et al., Gazz. Chim. Ital. 95, page 1338, (1965).

The use of hydrazoic acid or its derivatives creates a big problem in the industrial synthesis owing to the fact that their use involves the risk of explosion. Moreover the need for submitting the 17α-azido derivatives thus obtained to a subsequent catalytic reduction, make these processes more complicated and expensive.

According to the process which is the first object of the present invention, it has surprisingly been found that 16α-hydroxy-17α-aminopregnane derivatives of formula I can be obtained in very high yields simply through the direct action of ammonia or amines of formula $RNH_2$ wherein R is hydrogen, alkyl or aralkyl, on 16α,17α-epoxypregnanes of formula

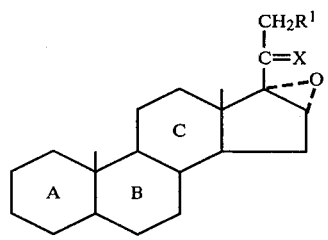

(II)

wherein $R^1$ has the same meanings given before, and rings A, B, and C may be substituted and bear double bonds as indicated above, and X is a N-containing protecting group of the keto function that may be easily removed in order to restore the keto function itself. Among the N-containing protecting groups of the C-20 keto function which may suitably be employed in this process, there are hydrazine and hydroxylamine derivatives. Those hydrazines of formula $H_2N-NR^4R^5$ wherein $R^4$ and $R^5$ are independently selected from the group consisting of hydrogen, aryl, alkanoyl, aralkanoyl, carboalkoxy and carboaralkoxy, are particularly useful. Said hydrazines, when reacted with the carbonyl group at the 20-position of the pregnane substrate form a group X represented by the following iminic portion $=N-NR^4R^5$ wherein $R^4$ and $R^5$ have the same meanings as before. These groups are easily removed, when the aminic function has been introduced at the 17-position, by hydrolysis of the corresponding 20-imino derivative with diluted acids. When the process of the present invention is employed for preparing pregnano[17α,16α-d]oxazoline derivatives, the hydrolytic treatment is preferably carried out on the pregnane derivative already containing the oxazoline ring, i.e., after the intermediate 16α-hydroxy 17α-aminopregnane of formula I wherein R is hydrogen, has been converted into the corresponding pregnano[17α,16α-d]oxazoline of formula III wherein the carbonyl group at the 20-position is protected. The introduction of hydrazine groups to protect the keto function at position 20 of the pregnane skeleton is described for example by B. Ellis et al., in J. Chem. Soc. 4111 (1961).

The 16α,17α-epoxypregnane derivatives, after introducing the aminic function at position 17α and, optionally, after converting them into pregnanooxazolines of formula III, can be modified further by means of suitable chemical or biological reactions widely known in the steroid chemistry, such as for instance the introduction of a hydroxy function at C-11, the introduction of a double bond at positions 1-2 and/or 4-5, the introduction of a keto function at C-3 and of an acyloxy group at C-21, when these functions are not present in the starting 16α,17α-epoxypregnane molecule. See for instance U.S. Pat. Nos. 3,461,119, 3,436,389 and 3,452,005.

Opening of 16α,17α-epoxides is generally carried out at a temperature comprising between 5° C. and 100° C., preferably between 10° C. and 35° C., in the presence of an amine of formula $RNH_2$ and, preferably, in the presence of an anhydrous aprotic organic solvent.

The reaction may take from a few minutes to several hours depending on the temperature and the amine employed. Organic solvents which are particularly useful in this reaction are for instance aromatic hydrocarbons such as benzene and toluene and their nitrogen containing isosters like pyridine and picolines, the alkoxy-lower alkane such as for instance dimethoxyethane, cyclic ethers such as tetrahydrofuran and dioxane, dimethylformamide, and dimethylsulfoxide.

The recovery of the reaction products, the 16α-hydroxy-17α-aminopregnane derivatives, does not present any particular difficulty.

In general, when the reaction is carried out in a water miscible organic solvent, the reaction product is preferably precipitated by dilution with water. The obtained precipitate is recovered by filtration and then, after being washed carefully, may be recrystallized from an organic solvent. The end crystallization may not be necessary if the obtained product undergoes further reactions, such as the conversion to pregnane-oxazoline. In some cases the reaction product is recovered by evaporating off the solvent to a small volume followed by precipitation optionally by the addition of non-solvents.

Conversion of the thus obtained 16α-hydroxy-17α-aminopregnane derivatives into pregnano[17α,16α-d]oxazolines and the corresponding further transformations are conveniently carried out by following the procedures described in U.S. Pat. Nos. 3,413,286, 3,461,119, 3,436,389, and 3,452,005.

A method particularly simple and effective for transforming the 16α-hydroxy-17α-amino pregnane derivatives into the corresponding oxazoline derivatives comprises treating at room temperature the amino derivative with a mixture of the anhydride of formula $(R^2CO)_2O$ and the corresponding acid or with a solution of the anhydride of formula $(R^2CO)_2O$ in dimethylformamide.

The reaction can be carried out directly on the solution deriving from the amination of the 16α,17α-epoxide.

The following examples describe in detail some particular aspects of the present invention but in no way they should be considered as a limitation to its scopes.

EXAMPLE 1

16α,17α-epoxy-3β-hydroxy-5α-pregna-11,20-dione 20-ethoxycarbonylhydrazone

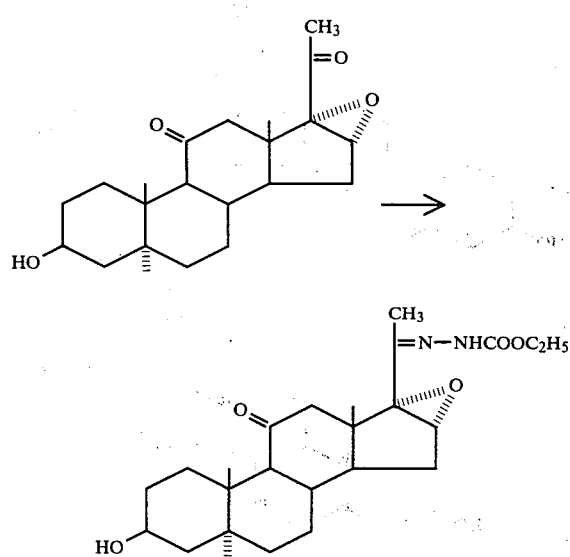

Ethyl hydrazinecarboxylate (18 g) first, and then a solution of conc. $H_2SO_4$ (0.75 g) in dioxane (18 ml) are added to a mixture of 16α,17α-epoxy-3β-hydroxy-5α-pregna-11,20-dione (18 g) in dioxane (180 ml).

The mixture is stirred for 48 hours at room temperature and then poured into ice-water (540 ml). The reaction product which precipitates is recovered by filtration, washed with water and dried yielding 21 g of the compound of the title sufficiently pure for the next step. This product crystallizes in two forms:

(A) m.p. 175°–79° C. (from ethyl acetate), $[α]_D = +103.6°$ (1% $CHCl_3$).

(B) m.p. 182°–85° C., which is obtained directly from water by carrying out the reaction as described above but adding methanol (50 ml) to the reaction mixture. In this case the reaction is complete in two hours at room temperature.

EXAMPLE 2

17α-amino-16α,3β-dihydroxy-5α-pregna-11,20-dione 20-ethoxycarbonylhydrazone

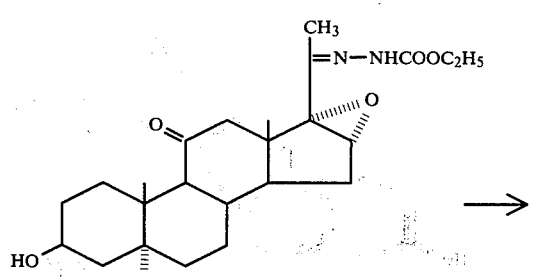

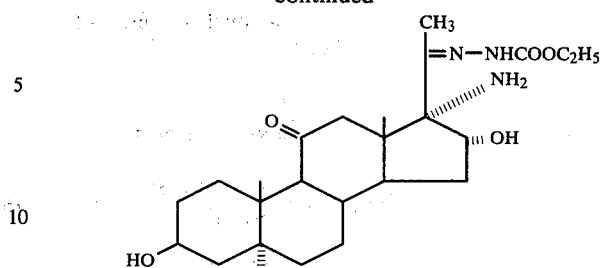

The compound of Example 1 (3 g) in pyridine (30 ml) is kept under a gentle flow of gaseous ammonia for 48 hours at room temperature, interrupting the flow during the night. The reaction mixture is then diluted with water (200 ml) while cooling with ice. The gummy solid which separates, is recovered by filtration, washed with water and dried yielding 2.7 g of the compound of the title as a solid product. M.p. 145°–60° C.

Upon crystallization from ethyl acetate the compound melts at 169°–74° C.; $[α]_D = -66°$ (1% MeOH).

Analogously the reaction can be carried out in dimethoxyethane (3 g in 75 ml) for 60 hours at room temperature giving the same results.

EXAMPLE 3

3β-hydroxy-5α-pregna-11,20-dione[17α,16α-d]-2'-methyl-oxazoline 20-ethoxycarbonylhydrazone

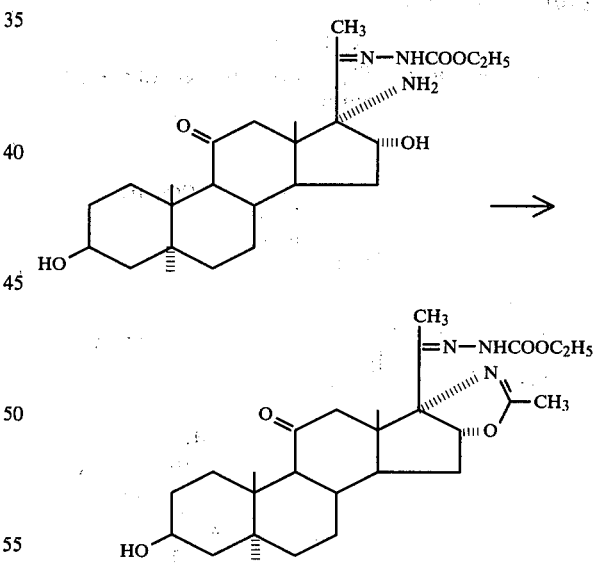

The compound of Example 2 (2 g) is added portionwise to a mixture of acetic acid (6 ml) and acetic anhydride (6 ml) and after 90 minutes at room temperature the reaction mixture is poured into water (60 ml). After the excess of acetic anhydride has been decomposed, the mixture is alkalinized with 4 N NaOH. The solid product is recovered by filtration, washed with water and dried yielding 2 g of the compound of the title. The compound purified by crystallization from ethyl acetate melts at 158°–62° C.; $[α]_D = +81.1°$ (1% $CHCl_3$).

EXAMPLE 4

3β-hydroxy-5α-pregna-11,20-dione[17α,16α-d]-2'-methyl-oxazoline

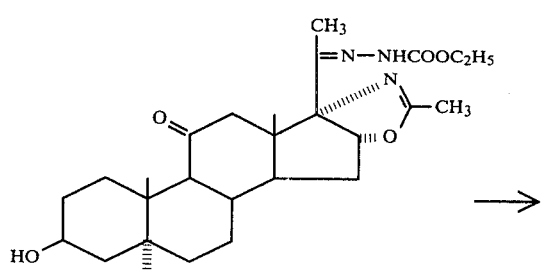

A suspension of the compound of Example 3 (1 g) in 10% HCl (10 ml) is stirred at room temperature for 15 hours. The reaction mixture is then brought to basic pH by the addition of 1 N NaOH, the solid is recovered by filtration, washed with water and dried yielding 0.70 g of the compound of the title which is purified by crystallization from ethyl acetate. M.p. 210°–212° C.; $[\alpha]_D = +103°$ (0.5% CHCl$_3$)

EXAMPLE 5

17α-amino-16α,3β-dihydroxy-5-pregnen-20-one-20-ethoxycarbonylhydrazone

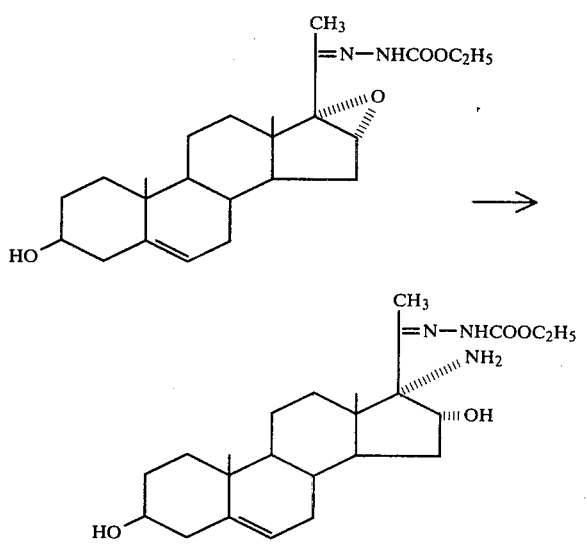

Gaseous ammonia is slowly bubbled into a solution of 16α,17α-epoxy-3β-hydroxy-5-pregnen-20-one 20-ethoxycarbonylhydrazone (10 g) in dimethylformamide (80 ml), kept at 20° C., during a period of 6 hours. The solution saturated with ammonia is set aside for 42 hours, then it is diluted with ice-water (1 l). After 30 minutes the precipitate is recovered by filtration (9.2 g) and washed with water. The product crystallized from ethyl acetate melts at 174°–76° C.; $[\alpha]_D = -146°$ (1% MeOH).

EXAMPLE 6

3β-hydroxy-5-pregnen-20-one[17α,16α-d]-2'-methyl-oxazoline 20-ethoxycarbonylhydrazone

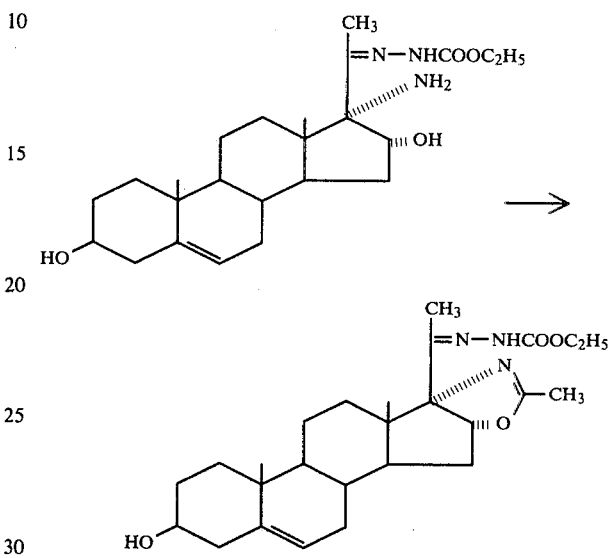

The compound of Example 5 (9.1 g) is stirred into a mixture of acetic acid (27.3 ml) and acetic anhydride (27.3 ml) at 20° C. After 1 hour the mixture is poured into ice-water (200 ml) and neutralized with concentrated NH$_4$OH. The solid precipitate is recovered by filtration, washed with water and dried yielding 9.6 g of the compound of the title which is purified by crystallization from ethyl acetate; m.p. 190°–193° C.; $[\alpha]_D = +17.4°$ (1%, CHCl$_3$).

EXAMPLE 7

3β-hydroxy-5-pregnen-20-one[17α,16α-d]-2'-methyl-oxazoline

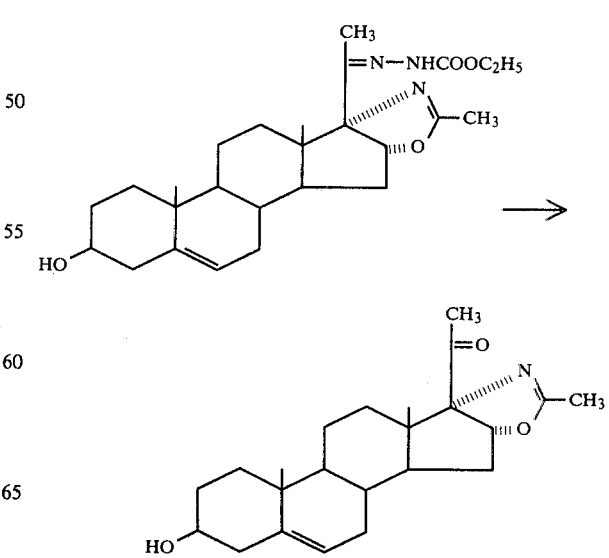

The raw 20-ethoxycarbonylhydrazone of Example 6 (9.0 g) is added to 10% HCl (100 ml) and kept under stirring at 20° C. for 18 hours. The reaction mixture is poured into water (220 ml) and, while cooling, it is brought to pH 9-10 by the addition of 10% aqueous NaOH. The solid is collected by filtration, washed with water and dried yielding 7.3 g of the compound of the title which is recrystallized from methanol/water 1/1—m.p. 195°-204° C.; $[\alpha]_D = +5.9°$ (1% CHCl$_3$).

EXAMPLE 8

17α-benzylamino-16α,3β-dihydroxy-5-pregnen-20-one 20-ethoxycarbonylhydrazone

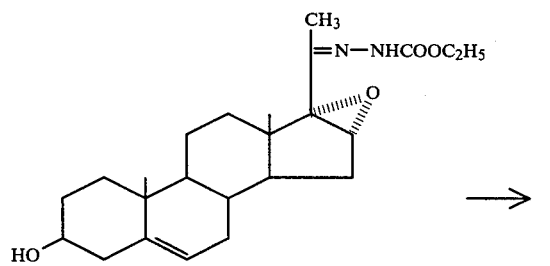

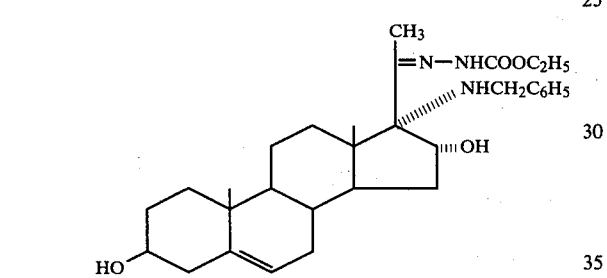

(a) Benzylamine (2 g) is added to 16α,17α-epoxy-3α-hydroxy-5-pregnen-20-one 20-ethoxycarbonylhydrazone (2 g) in dimethoxyethane (30 ml) and the reaction mixture is heated to 60° C. for 3½ hours. The reaction mixture is set aside overnight and then it is diluted with water (150 ml). The gummy product is recovered by decantation and triturated with additional water giving 2.2 g of the compound of the title; m.p. 115°-25° C.

(b) Analogously, a suspension of 16α,17α-epoxy-3β-hydroxy-5-pregnen-20-one 20-ethoxycarbonylhydrazone (2 g) and benzylamine (2 g) in toluene (50 ml) is heated to 65° C. for five hours (a clear solution forms and then the reaction product precipitates).

After standing at 20° C. overnight, the solid is recovered by filtration yielding 2.2 g of the compound of the title. M.p. 125°-28° C.; $[\alpha]_D = -123.2°$ (1% CHCl$_3$).

EXAMPLE 9

16α,17α-epoxy-3β-acetoxy-5-pregnen-20-ene-20-ethoxycarbonyl hydrazone

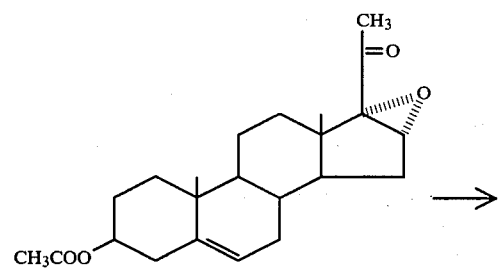

-continued

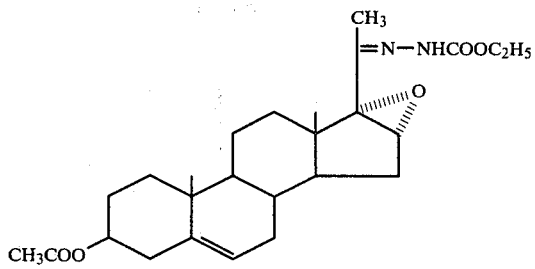

Ethyl hydrazinecarboxylate (7 g) first and then a solution of concentrated H$_2$SO$_4$ (0.25 ml) in dioxane (10 ml) are added to a solution of 3β-acetoxy-16α,17α-epoxy-5-pregnen-20-one (10 g) in dioxane (100 ml). Methanol (30 ml) is then added and the obtained reaction mixture is allowed to stand at room temperature for two hours. The reaction mixture is then diluted by slowly adding ice-water (420 ml). The precipitate which separates is recovered by filtration, washed with water and dried giving 12.3 g of the compound of the title; m.p. 211°-212° C.

EXAMPLE 10

3β-acetoxy-17α-amino-16α-hydroxy-5-pregnen-20-one 20-ethoxycarbonylhydrazone

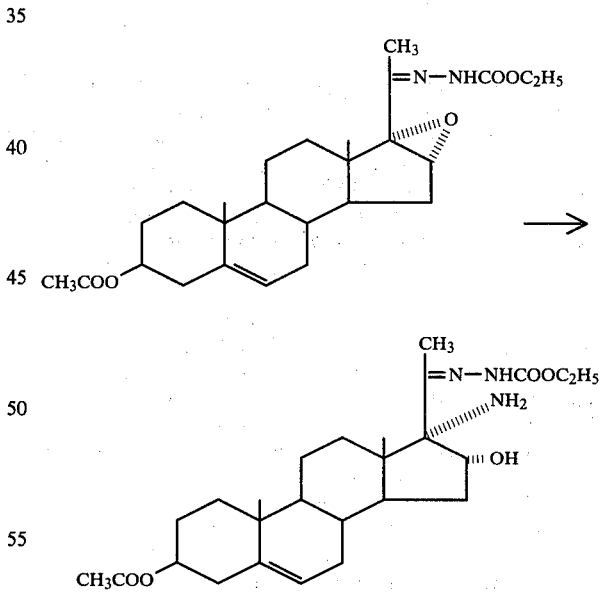

Gaseous ammonia is bubbled into a suspension of the compound of Example 9 (2.29 g) in dimethylformamide (23 ml), for 48 hours at room temperature. The reaction mixture is then diluted, while cooling, with water (50 ml) and the obtained solid is collected by filtration. Yield: 2.23 g. The compound crystallized from 95% ethanol, melts at 287°-89° C.; $[\alpha]_D = -123°$ (1% CHCl$_3$).

EXAMPLE 11

3β-hydroxy-5-pregnen-20-one-[17α,16α-d]-2'-methyloxazoline

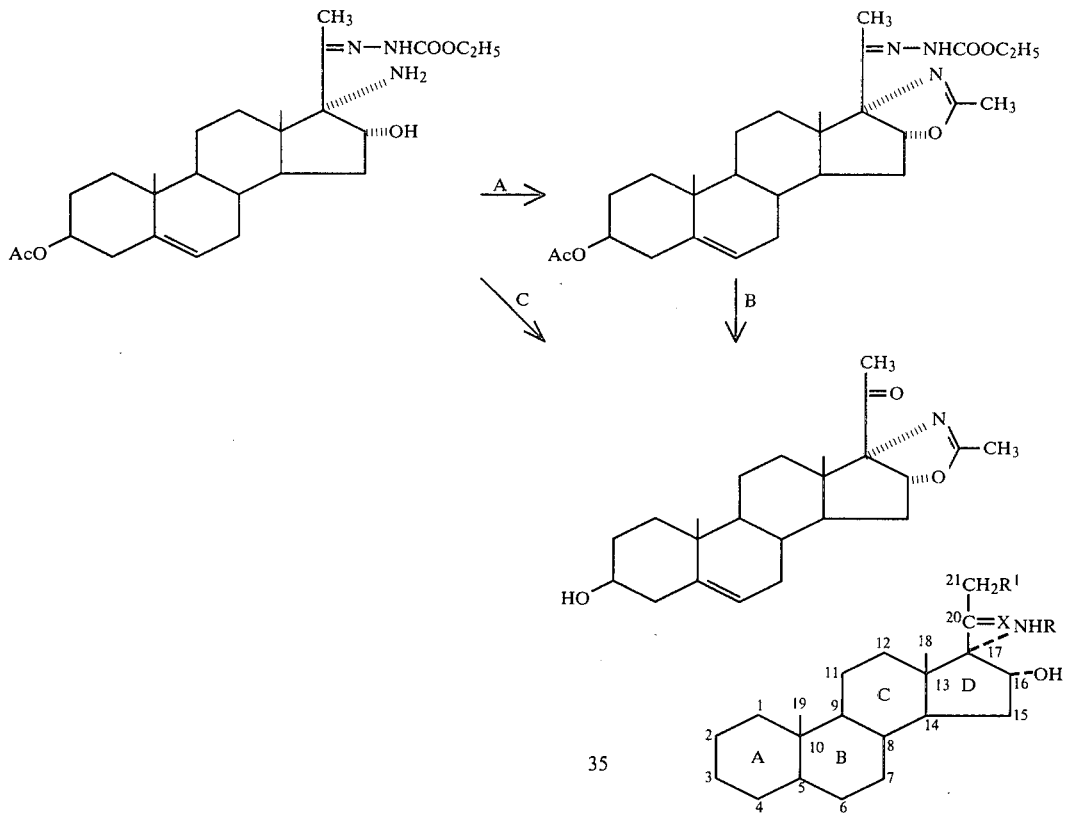

(A) The compound of Example 10 (3 g) is added portionwise to a mixture of acetic acid (15 ml) and acetic anhydride (3 ml). The reaction mixture is stirred at room temperature for 3 hours and then diluted with ice-water (50 ml). After one hour the reaction mixture is cooled and alkalinized by the addition of concentrated NH4OH. The obtained solid product is collected by filtration, washed and dried, yielding 3 g; m.p. 245°–48° C.; $[\alpha]_D = +5.7°$ (1% CHCl3).

(B) A mixture of the compound obtained in step (A) above (2.5 g) in 10% HCl (25 ml) is stirred at 20° C. for 20 hours. Then the reaction mixture is diluted with ice-water (25 ml) and the obtained suspension is alkalinized by the addition of concentrated NH4OH. The solid which precipitates is collected by filtration yielding 1.8 g of the compound of the title. M.p. 195°–201° C.

(C) The compound of Example 10 (6 g) is reacted, as described in Step (A) above, with a mixture of acetic acid (30 ml) and acetic anhydride (6 ml) for 3 hours. While controlling the temperature, 12% HCl (40 ml) is slowly added, then the reaction mixtures is heated to 40° C. for 8 hours and allowed to stand at room temperature for additional 16 hours. After this time, the reaction mixture is diluted with ice-water (100 ml) and alkalinized with concentrated NH4OH. The solid product is filtered, washed and dried yielding 3.98 g of the compound of the title; m.p. 193°–200° C.

I claim:

1. A process for preparing 16α-hydroxy-17α-aminopregnane derivatives represented by the following general formula (I)

wherein R is hydrogen, alkyl, aralkyl; R[1] is hydrogen hydroxy, alkanoyloxy, or aroyloxy, X is O or an easily removable hydrazine or hydroxylamine protecting group for the carbonyl function, rings A, B, C of the pregnane skeleton may be substituted at the 3- and 11-positions with oxo, hydroxy, alkoxy, aralkoxy and acyloxy groups and bear one or more noncumulated double bond at the 1-2, 3-4, 4-5, 5-6, and 6-7, and 9-11 positions, charcterized in that a compound of formula

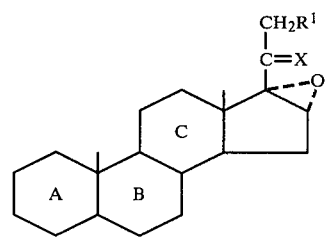

(II)

wherein R[1] has the same meanings as above, rings A, B, and C may be substituted and bear double bonds as described above, and X is a N-containing protecting group of the keto function which may be easily removed in order to restore the keto function itself, is contacted with an amine of formula RNH2 wherein R is hydrogen, alkyl or aralkyl and, when a compound of formula I is desired wherein X is oxygen, the N-containing protecting group is removed to restore the keto function.

2. A process as in claim 1 wherein the N-containing protecting group of the keto function X is an imino group of the formula =N—NR⁴R⁵ wherein R⁴ and R⁵ each independently are selected from hydrogen, aryl, alkanoyl, aralkanoyl, carboalkoxy, and carboaralkoxy.

3. A process as in claims 1 or 2 wherein the compound of formula II and the amine RNH₂ are contacted at a temperature comprised between 5° C. and 100° C. in the presence of an aprotic organic solvent.

4. A process as in claim 3 wherein the solvent is selected from benzene, toluene, pyridine, picoline, dimethoxyethane, tetrahydrofuran, dioxane, dimethylformamide and dimethylsulfoxide.

5. A process as in claim 1 wherein an excess of the amine RNH₂ is employed.

6. A process according to claim 1 wherein the compounds have the following structures

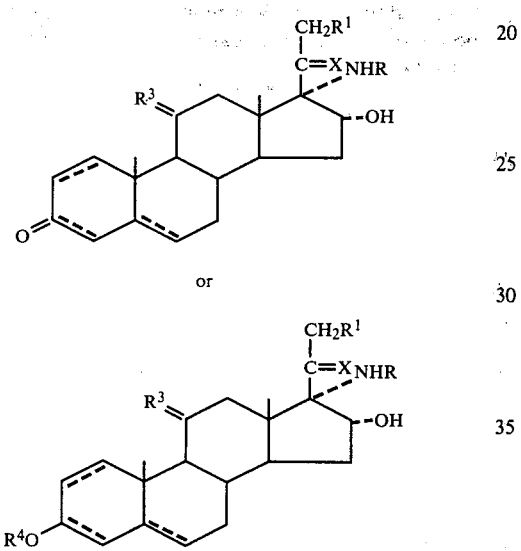

or

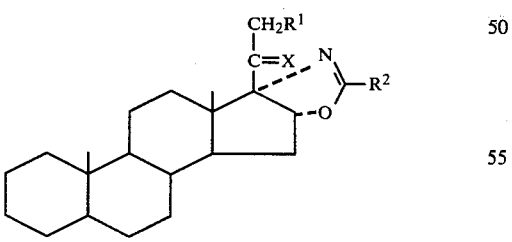

wherein R, R¹ and X have the same meanings as in claim 1, R³ represents H₂, O, H(OH) or H(O-acyl), and R⁴ represents H, alkyl, aralkyl or acyl and the dotted lines represent optional double bonds between the adjacent carbon atoms of the pregnane skeleton.

7. A process for the preparation of pregnano[17α,16α-d]oxazoline derivatives having the formula

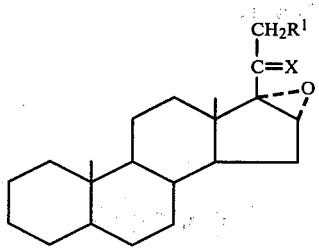

wherein R¹ is hydrogen, hydroxy, alkanoyloxy, aroyloxy, carboalkoxy or carboaralkoxy; R² is alkyl, aryl, or aralkyl; X is O or an easily removable protecting group of the carbonyl function, rings A, B, C are substituted at C-3 with an oxo, hydroxy, alkoxy, aralkoxy or acyloxy group, may be substituted at C-11 with a group selected from oxo, hydroxy and acyloxy, and may bear one or more non-cumulated double bonds at the 1-2, 3-4, 4-5 and 5-6 positions, which comprises:

(a) contacting a 16α,17α-epoxypregnane, having the formula

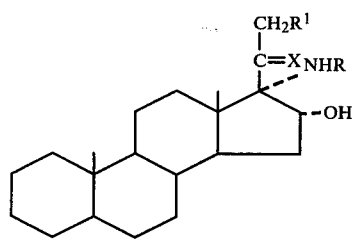

wherein R¹ and X are as described above with an amine of the formula RNH² wherein R is alkyl or aralkyl to form a 16α-hydroxy-17α-aminopregnane derivative having the formula

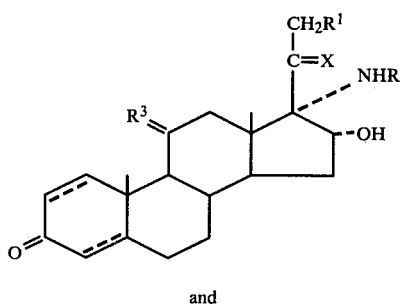

wherein R¹ and X are as described above and R is alkyl or aralkyl;

(b) treating said 16α-hydroxy-17α-aminopregnane derivative with a mixture of an anhydride having the formula (R²CO)₂O, wherein R² is as defined above, and the corresponding acid;

(c) removing the carbonyl protecting group, if any; and (d) isolating the desired pregnano[17α,16α-d]oxazoline derivative therefrom.

8. A process according to claim 7 wherein the 16α-hydroxy-17α-aminopregnane derivatives prepared are

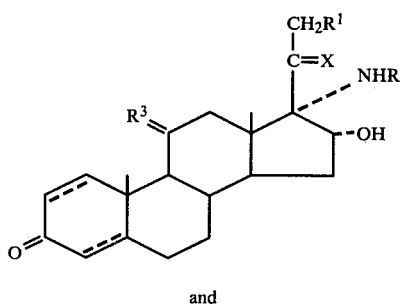

and

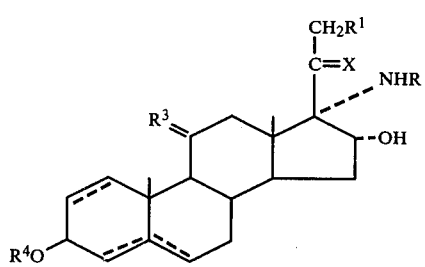

wherein R, R¹, X, R³, R⁴ and the dotted lines are defined as in claim 6.

9. A 16α-hydroxy-17α-amino-pregnane derivative having the formula

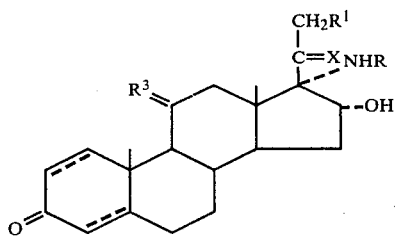

or

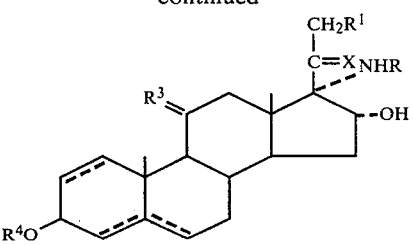

wherein R is alkyl or aralkyl; $R^1$ is selected from the group consisting of hydrogen, hydroxy, alkanoyloxy and aroyloxy; X is oxygen or an easily removable nitrogen containing protecting group of the carbonyl function; $R^3$ is selected from the group consisting of hydrogen, oxygen, H(OH) and H(O-Acyl); $R^4$ is selected from the group consisting of hydrogen, alkyl, aralkyl or acyl; and the dotted lines represent optical double bonds between the adjacent carbon atoms of the pregnane skeleton.

* * * * *

UNITED STATES PATENT AND TRADEMARK OFFICE
CERTIFICATE OF CORRECTION

PATENT NO. : 4,412,953

DATED : November 1, 1983

INVENTOR(S) : Giorgio Winters

It is certified that error appears in the above-identified patent and that said Letters Patent are hereby corrected as shown below:

At column 2, line 44, the patent reads "O H(OH)," and should read
-- O, H(OH), --.

At column 9, line 37, the patent reads "epoxy-3α-" and should read
-- epoxy-3β- --.

At column 9, line 55, the patent reads "pregnen-20-ene-20-" and should read
-- pregnen-20-one 20- --.

Signed and Sealed this

Twenty-fifth Day of October, 1988

*Attest:*

DONALD J. QUIGG

*Attesting Officer*   *Commissioner of Patents and Trademarks*